United States Patent [19]
Li et al.

[11] Patent Number: 6,057,928
[45] Date of Patent: May 2, 2000

[54] FREE-SPACE TIME-DOMAIN METHOD FOR MEASURING THIN FILM DIELECTRIC PROPERTIES

[75] Inventors: Ming Li, Troy; Xi-Cheng Zhang, Latham; Gyu Cheon Cho, Albany, all of N.Y.

[73] Assignee: Rensselaer Polytechnic Institute, Troy, N.Y.

[21] Appl. No.: 09/333,596

[22] Filed: Jun. 15, 1999

[51] Int. Cl.[7] .................................................. G01N 21/55
[52] U.S. Cl. .......................................... 356/445; 356/361
[58] Field of Search ..................................... 356/445, 361

[56] References Cited

U.S. PATENT DOCUMENTS

| | | | |
|---|---|---|---|
| 4,968,136 | 11/1990 | Lim et al. | 356/350 |
| 5,034,617 | 7/1991 | Isobe | 250/560 |
| 5,056,111 | 10/1991 | Duling, III et al. | 375/37 |
| 5,376,888 | 12/1994 | Hook | 324/643 |
| 5,381,234 | 1/1995 | Barbee et al. | 356/369 |
| 5,502,392 | 3/1996 | Arjavalingam et al. | 324/638 |
| 5,548,404 | 8/1996 | Kupershmidt et al. | 356/368 |
| 5,726,578 | 3/1998 | Hook | 324/643 |
| 5,798,837 | 8/1998 | Aspnes et al. | 356/369 |
| 5,818,582 | 10/1998 | Fernandez et al. | 356/318 |
| 5,872,447 | 2/1999 | Hager, III | 324/71.1 |
| 5,889,592 | 3/1999 | Zawaideh | 356/349 |
| 5,946,096 | 8/1999 | Lee et al. | 356/349 |

OTHER PUBLICATIONS

"Optoelectronic Transient Characterization of Ultrafast Devices" by M.Y. Frankel et al. IEEE Journal of Quantum Electronics, vol. 28, No. 10. Oct. 1992. pp. 2313–2324.

"Optoelectronic On–Chip Characterization of Ultrafast Electric Devices: Measurement Techniques and Applications" by T. Pfeifer et al. IEEE Journal of Selected Topics in Quantum Electronics. vol. 2, No. 3, Sep. 1996. pp. 586–603.

"Coherent broadband microwave spectroscopy using picosecond optoelectronic antennas" by Y. Pastol et al. Appl. Phys. Lett. 54(4), Jan. 23, 1989. pp. 307–309.

"Far–infrared time–domain spectroscopy with terahertz beams of dielectrics and semiconductors" by D. Grischkowsky et al. J. Opt. Soc. Am. B/vol. 7, No. 10. Oct. 1990. pp. 2006–2015.

"A Reliable Method for Extraction of Material Parameters in Terahertz Time–Domain Spectroscopy" by L. Duvillaret et al. IEEE Jor. Sel. Top. in Quantum Elec. Sep. 1996. pp. 739–745.

"Gas spectroscopy measurements using a compact terahertz system" by G. Sucha et al. Proceedings of VSJ–SPIE98. Dec. 6, 1998. pp. 1–3.

"Design and Characterization of Traveling–Wave Electrooptic Terahertz Sensors" by Q. Wu et al. IEEE Jour. Sel. Topics in Quantum Elec. vol.. 2, No.3, Sep. 1996. pp. 693–700.

"Principles of Optics" 6th Ed. by M. Born et al. 1980. pp 38–41.

Primary Examiner—Robert H. Kim
Assistant Examiner—Phil Natividad
Attorney, Agent, or Firm—Ratner & Prestia

[57] ABSTRACT

A non-contact method for determining the index of refraction or dielectric constant of a thin film on a substrate at a desired frequency in the GHz to THz range having a corresponding wavelength larger than the thickness of the thin film (which may be only a few microns). The method comprises impinging the desired-frequency beam in free space upon the thin film on the substrate and measuring the measured phase change and the measured field reflectance from the reflected beam for a plurality of incident angles over a range of angles that includes the Brewster's angle for the thin film. The index of refraction for the thin film is determined by applying Fresnel equations to iteratively calculate a calculated phase change and a calculated field reflectance at each of the plurality of incident angles, and selecting the index of refraction that provides the best mathematical curve fit with both the dataset of measured phase changes and the dataset of measured field reflectances for each incident angle. The dielectric constant for the thin film can be calculated as the index of refraction squared.

11 Claims, 5 Drawing Sheets

FREE-SPACE TIME-DOMAIN METHOD FOR MEASURING THIN FILM DIELECTRIC PROPERTIES

TECHNICAL FIELD

The present invention relates generally to measurement of dielectric properties of thin films on substrates and, more specifically, to determination of the index of refraction and the dielectric constant of a thin polymer film on a silicon substrate in the gigahertz (GHz)–terahertz (THz) frequency range.

BACKGROUND OF THE INVENTION

In modern microcircuits, the high-frequency capacitance of interlevel dielectrics is a critical parameter that must be understood for realization of high-speed (clock speed>1 GHz) electronic devices. The characterization of the high-frequency dielectric properties of interlevel dielectrics is thereby crucial. To bridge electronic and optical gaps formerly encountered in the measurement of the dielectric constant in the GHz–THz frequency range, time-domain optoelectronic techniques that incorporate ultrashort laser pulses have been developed in recent years for microcircuit test devices.

For characterization of low dielectric constant materials before circuitization, however, a free-space, non-contact measurement is the most convenient and low-cost method. For this purpose, a time-domain coherent technique has been demonstrated in the far-infrared (FIR) range that has been shown to be a promising alternative to the conventional electronic or continuous wave method. Boosted by the rapid development of a compact and portable femtosecond (fs) laser system, time-domain FIR techniques using all room-temperature components have become attractive for a number of industrial applications, including, but not limited to, gas spectroscopy, measurement of conductivity, study of the dynamics of semiconductor materials, and measurement of water concentration in biological samples. With extremely flat frequency response, large dynamic range, and excellent signal-to-noise ratio (SNR), free-space electro-optic sampling (FS-EOS) has emerged as a coherent terahertz detection technique capable of detecting amplitude, phase, and spacial distribution information in a terahertz beam. For example, the refractive index and dielectric constant of thin films has been measured by inserting the film into a THz beam and comparing the Fourier transforms of the THz waveforms obtained with and without the thin film.

For free-space dielectric constant measurement of the film on a substrate, where the thickness of the film is much thinner than the wavelength of the applied electromagnetic (EM) waves, the free-space time-domain technique has a fundamental restriction. The principle of the coherent free-space technique for measurement of the dielectric constant is based on the evaluation of the relative phase shift due to the index of refraction, the index of refraction being the square-root of the dielectric constant. For a film thinner than the wavelength used for measurement, the visibility of the small phase shift in the waveform is difficult to obtain under realistic experimental conditions. For instance, for 100 GHz EM waves refracted through a one-micrometer film, a phase change on an order of only $10^{-3}$ radians is expected. This phase difference is extracted by comparing a first waveform refracted through the thin film on a substrate against a second, reference waveform reflected from the substrate without the film. Under most experimental conditions, this extraction is often difficult due to the experimental uncertainty between two separate measurements. Thus, it is highly desirable to measure the phase difference in a single measurement.

SUMMARY OF THE INVENTION

The present invention provides a non-contact method for determining the index of refraction and dielectric constant of a thin film on a substrate at a desired frequency having a corresponding wavelength larger than a thickness of the thin film. The method comprises simultaneously impinging a desired-frequency beam and a reference beam upon the thin film on the substrate at an incident angle in free space, creating a reflected output desired-frequency beam and a reflected output reference beam from the input beams. The input beams are impinged over a plurality of delay times between the input beams such that a complete waveform of the reflected output desired-frequency beam may be characterized.

Next, the method comprises measuring both a measured phase change and a measured field reflectance from the complete waveform of the reflected desired-frequency beam at the incident angle with respect to a complete waveform of the input desired-frequency beam. These steps are repeated for a plurality of incident angles in a range of angles encompassing the Brewster's angle for the thin film, thus creating a first data set of measured phase changes and a second data set of measured field reflectances. The index of refraction for the thin film is determined by iteratively calculating both a calculated phase change and a calculated field reflectance at each of the plurality of incident angles for one or more indices of refraction, and selecting the index of refraction that provides the best mathematical curve fit with the first and second data sets. The calculated phase change and calculated field reflectance are calculated using a set of Fresnel equations provided in the detailed description.

The method of the present invention is particularly useful in the far infrared (FIR) range, meaning that the desired frequency generally corresponds to a wavelength longer than about 7 microns. Specifically, this method is useful where the desired frequency is in the gigahertz (GHz) to terahertz (THz) range, particular those frequencies having a corresponding wavelength in the range of about 0.1 millimeter to about 1 centimeter. The method may be used for measuring thin films having a thickness of only a few microns or less.

The method of this invention may be specifically conducted by creating first and second laser pulses. The first pulse is an excitation pulse that travels through a variable-length delay stage and impinges upon an emitter that becomes excited and emits the desired-frequency beam having a "p" polarization. The second pulse is the reference beam comprising a probe pulse that has an "s" polarization. The reflected reference beam and the reflected desired-frequency beam (as reflected off the sample) are then impinged upon an electro-optical sensor that modulates the reflected probe pulse by the reflected desired-frequency beam to create an electro-optical (EO) resultant having a linear polarization. The EO resultant is circularly polarized with a quarter waveplate and then linearly polarized with a Wollaston prism that splits the resultant into a first beam having s plus p components and a second beam having s minus p components. A first photo detector detects the first beam and a second photo detector detects the second beam, each photo detector converting the detected beam to electronic information.

The electronic information from the second detectable beam is subtracted from the electronic information from the first detectable beam, resulting in noise-reduced information regarding the p-polarized component, which is stored. The pulses are repeated for a plurality of lengths of the delay stage until the stored noise-reduced information corresponds to the complete waveform of the reflected desired-frequency beam. Then, a Fourier transform of the stored, noise-reduced, electronic information corresponding to the complete waveform of the output reflected desired-frequency beam is calculated and converted to polar coordinates for computation of the measured field reflectance and the measured phase change with respect to the Fourier transform (converted to polar coordinates) of the complete waveform of the input desired-frequency beam.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The present invention exploits the phase flip of electromagnetic (EM) waves of near-Brewster angle reflection from two interfaces by measuring the direct waveform difference of an FIR pulse induced by the phase shift in a thin film layer. The Brewster angle is the angle of incidence to a particular medium at which the reflectance is zero for a particular wavelength. The tangent of the Brewster angle is equal to the ratio of the refractive indices between the media of incidence and refraction.

Figure 1:
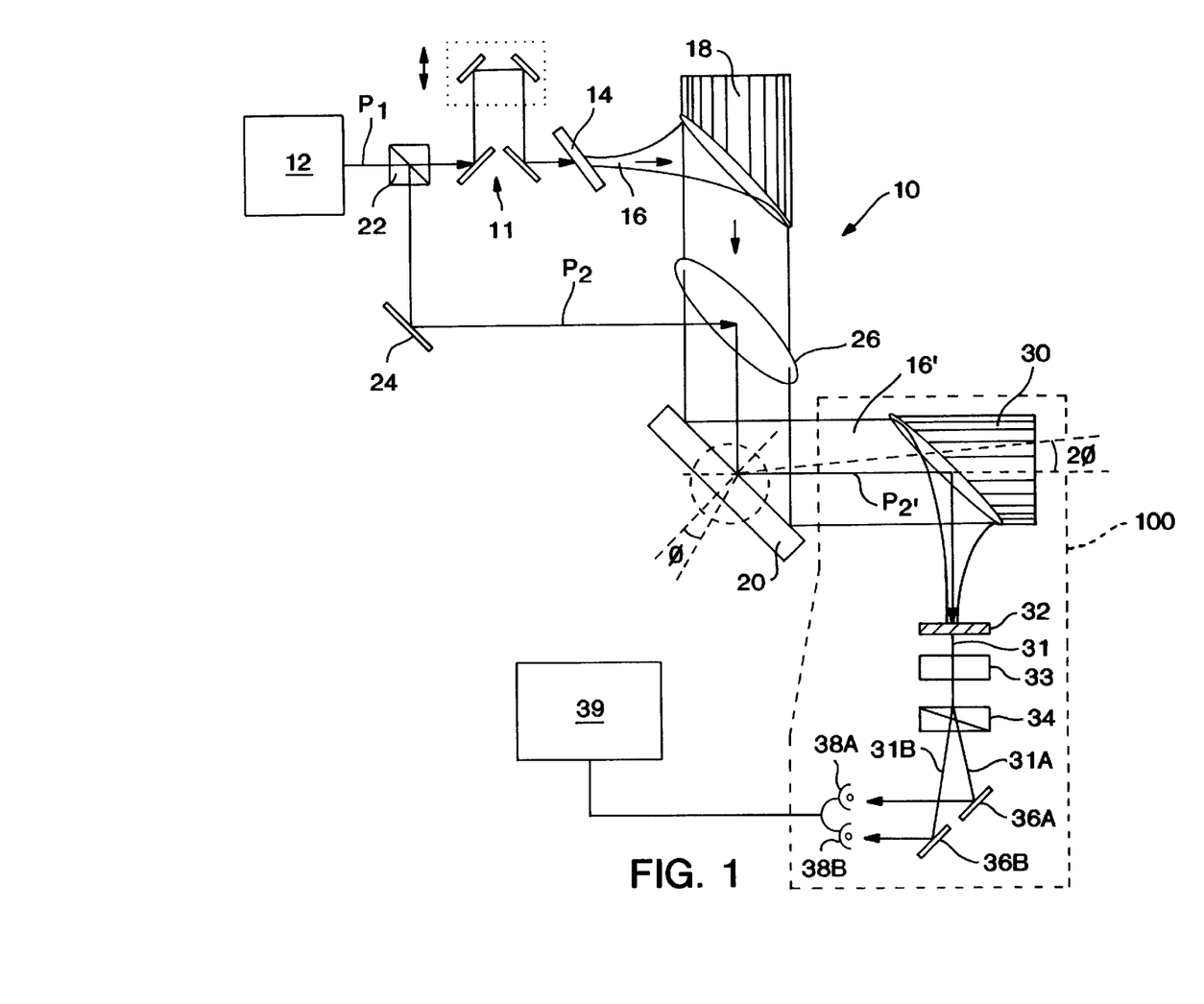
FIG. 1 is a schematic illustration of an exemplary system for performing the method of the present invention.

Referring now to the drawing, wherein like reference numbers refer to like elements throughout, FIG. 1 schematically shows an exemplary apparatus 10 for measuring the FIR dielectric constant of a thin film on a substrate. As depicted in FIG. 1, an optical source 12, such as a mode-locked titanium:sapphire laser, generates an illuminating optical excitation pulse $P_1$ onto emitter 14, which generates a beam of desired frequency. Emitter 14 may comprise, for example, an InGaAs surface-field layer that, when excited by pulse $P_1$, emits a p-polarized THz radiation beam 16. Pulse $P_1$ may be, for example, a 100-fs pulse that may impinge upon emitter 14 at an incidence angle for optimal emission of the desired-frequency wave such as, for instance, at an angle of 72 degrees for an emitter with an InGaAs surface-field layer.

Between optical source 12 and emitter 14, pulse $P_1$ is directed through delay stage 11, which provides a variable distance through which pulse $P_1$ can travel. Emitter 14 emits p-polarized radiation beam 16 of a desired-frequency, such as FIR GHz–THz radiation, onto a first paraboloidal mirror 18, which collimates desired-frequency radiation beam 16 and directs it toward sample 20. Reference pulse $P_2$ may be obtained by splitting pulse $P_1$ with a beam splitter 22 and reflecting pulse $P_2$ off mirror 24 to a pellicle 26. Pulse $P_2$ is an s-polarized beam. Pellicle 26 is typically 2 to 4 microns thick such that the long wavelength of radiation beam 16 allows it to pass through pellicle 26 without reflection. Pellicle 26 reflects pulse $P_2$ onto sample 20 along the same axis as radiation beam 16.

Radiation beam 16 and reference pulse $P_2$ reflect off sample 20 as reflected beam 16' and reflected pulse $P_2$'. Using a second paraboloidal mirror 30, reflected beam 16' and reflected pulse $P_2$' are focused onto an electro-optical (EO) sensor 32, such as a ZnTe crystal with a thickness of about 2 mm. In EO sensor 32, the E-field of reflected beam 16' tunes reflected pulse $P_2$' by modulating it to include a p-polarized component proportional to reflected beam 16'. Thus, beam 31 leaving EO sensor 32 is an optical beam having a waveform incorporating s+p components.

Quarter waveplate 33 changes the linear polarization of beam 31 to a circular polarization. Wollaston prism 34 splits the circular polarization of beam 31 back into linearly polarized beam 31A, having a waveform incorporating s+p components, and linearly polarized beam 31B, having a waveform incorporating s–p components. Each beam 31A and 31B is reflected off a mirror 36A and 36B, respectively, onto photo detectors 38A and 38B, respectively, which may be photodiodes. The information recorded by photo detectors 38A and 38B is processed by data acquisition system 39, such as a computer, which subtracts the waveform of beam 31B from the waveform of beam 31A to eliminate the s-component and, therefore, to isolate the p-component with reduced noise.

Figure 2:
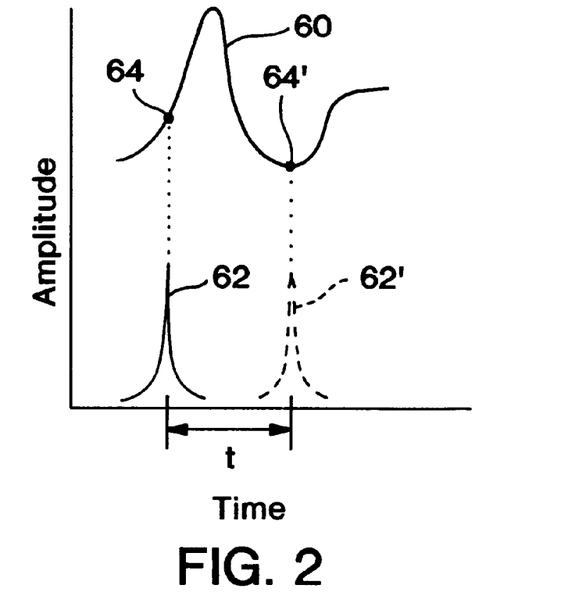
FIG. 2 is a plot of exemplary waveforms corresponding to the desired-frequency beam and the reference beam, showing the effect of changing the delay between the beams.

Referring now to FIG. 2, there are shown an exemplary waveform 60 corresponding to reflected beam 16' (having a long, GHz–THz wavelength) and waveforms 62 and 62' corresponding to reflected pulse $P_2$' (having a shorter, typically optical, wavelength). The wavelength of reflected pulse $P_2$' as modulated by reflected beam 16' in EO sensor 32 to include a p-component and as split by prism 34 into s+p and s−p beams 31A and 31B, respectively, is the wavelength actually detectable by photo detectors 38A and 38B. Therefore, the information detected for any given length of delay stage 11 is limited to the information contained in the wavelength of reflected pulse $P_2'$. Because the wavelength of reflected pulse $P_2'$ (as illustrated by waveform 62 in FIG. 2) is much shorter than the wavelength of reflected beam 16' (as illustrated by waveform 60 in FIG. 2) corresponding to the desired frequency to be studied, the p-information contained in waveform 62 is only representative of a single point 64 on waveform 60. By changing the pathlength of excitation pulse $P_1$, such as by varying the length of delay stage 11, the time-domain alignment of waveform 60 with respect to waveform 62 may be offset by a time delay, τ, as depicted by dashed waveform 62', thus providing another point 64' along waveform 60. Time delay τ is equal to Δl/c, where Δl is the change in optical path length and c is the speed of light.

Thus, information regarding the entire waveform 60 of reflected beam 16' is obtained by changing the time delay between reflected beam 16' and reference reflected pulse $P_2'$ over a plurality of lengths of delay stage 11 until a complete waveform 60 is characterized and stored electronically for a particular incident angle. The same information may be similarly derived by transmitting reference pulse $P_2$ through variable-length delay stage 11 instead of excitation pulse $P_1$.

This process is then repeated for the same delay stage positions for a plurality of incident angles. Sample 20 and the portion of apparatus 10 depicted in dashed box 100 of FIG. 1 are mounted on rotational stages (not shown) to obtain waveforms at a plurality of incident angles. The apparatus portion depicted in dashed box 100 must be rotated by 2ϕ for a sample rotation angle of ϕ, so that the components in box 100 are aligned to receive the reflected beams from sample 20.

Figure 3:
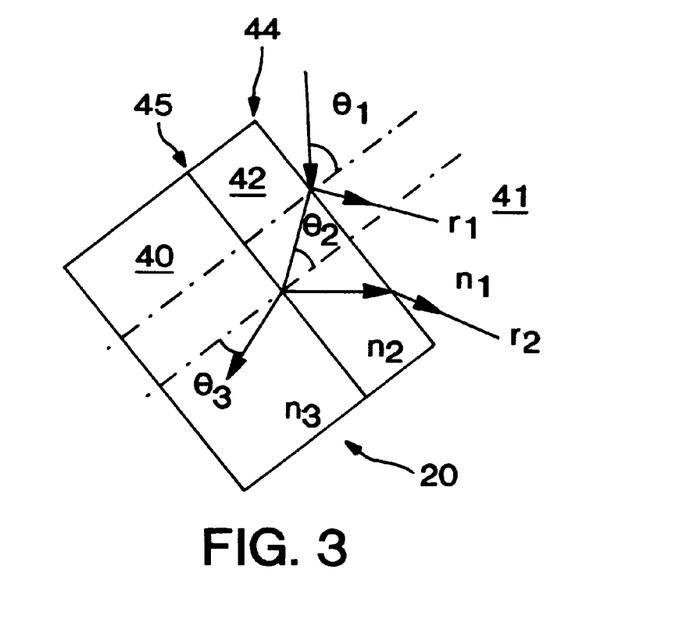
FIG. 3 is a schematic cross-sectional illustration of the encircled portion of the sample in FIG. 1, showing a substrate having a thin film layer and depicting incident and refractive angles of radiation impinged on the layer and substrate.

Referring now to FIG. 3, which is a cross-sectional schematic illustration of the encircled portion of sample 20 in FIG. 1, sample 20 essentially comprises a substrate 40 having thin film 42 on substrate 40. The indices of refraction for air 41, thin film 42, and substrate 40 are denoted by $n_1$, $n_2$, and $n_3$, respectively. The angles $\theta_1$ and $\theta_2$ are the incidence angles of the radiation on the air-to-film interface 44 and on the film-to-substrate interface 45, respectively. The angle $\theta_3$ corresponds to the refraction angle into substrate 40. Reflectances $r_1$ from interface 44 and $r_2$ from interface 45 are also indicated. Because the beam reflected by interface 45 is partially reflected by interface 44 back to interface 45 and back again to interface 44 multiple times, with a certain portion of each reflection passing through interface 44 each time, $r_2$ actually includes multiple reflection components not depicted in FIG. 3.

Figure 4A:
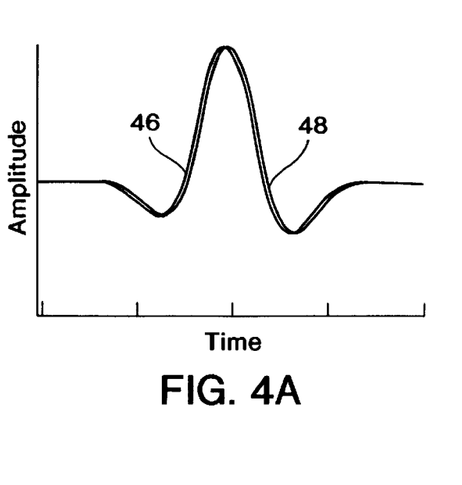
FIGS. 4A and 4B are graphs of time versus amplitude depicting the difference in the visibility of a phase change of two slightly phase-shifted (0.2 radian) waveforms and the superposition of those waveforms (at 0.5× magnification), respectively, of non-Brewster angle reflections from two interfaces having different indices of refraction.
Figure 4B:
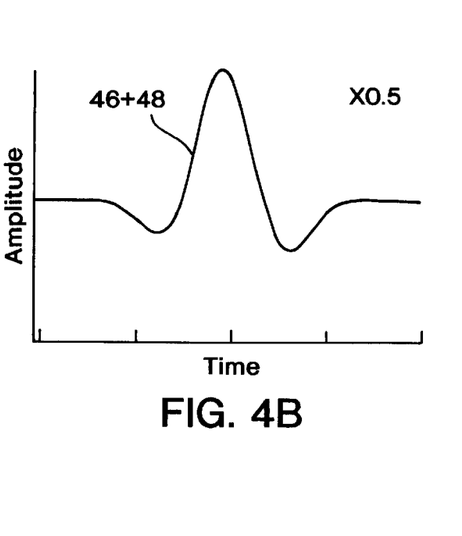

A direct observation of the phase shift caused by thin film 42 is possible for the Brewster angle reflection. FIGS. 4A, 4B, 5A, and 5B illustrate the waveform difference between a Brewster angle reflection and a non-Brewster angle reflection for thin film 42 with two interfaces. For simplicity, multiple reflection is neglected in these conceptual figures. FIG. 4A illustrates waveforms 46 and 48 reflected from the two interfaces, such as interfaces 44 and 45 in FIG. 3, at a non-Brewster angle. FIG. 4B illustrates the superimposition of waveforms 46 and 48 (shown at 0.5× magnification relative to FIG. 4A for illustrative purposes). As illustrated, the phase change between the waveforms 46 and 48 in FIG. 4A and FIG. 4B is difficult to discern.

Figure 5A:
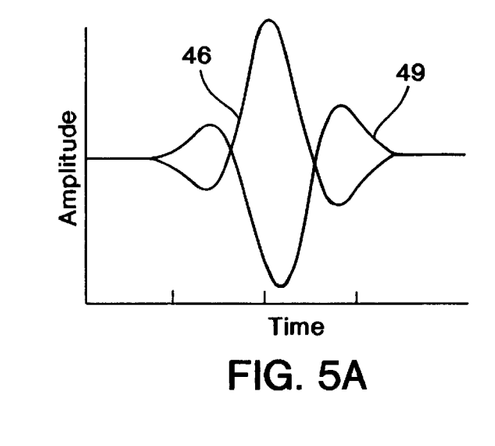
FIGS. 5A and 5B are graphs of time versus amplitude depicting the difference in the visibility of a phase change of two slightly phase-shifted (0.2 radian) waveforms and the superposition of those waveforms (at 5× magnification), respectively, of near-Brewster angle reflections from two interfaces having different indices of refraction.
Figure 5B:
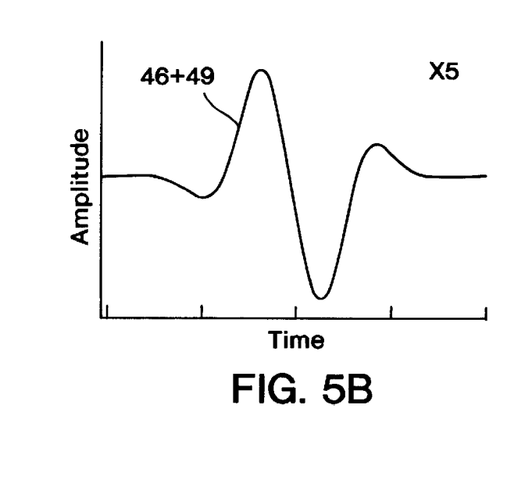

If, however, the incidence angle is larger than the Brewster angle of one interface but not larger than the Brewster angle at the other interface, then waveforms 46 and 49 have a phase flip with respect to one another, as shown in FIG. 5A. The superimposition of reflected waveforms 46 and 49 forms a direct waveform difference as shown in FIG. 5B (shown magnified 5 times, or 5×, relative to FIG. 5A for illustrative purposes). Thus, the phase change caused by thin film 42 is clearly visible and measurable from a single waveform. Evaluation of the single waveform eliminates errors introduced by recording a first, reference waveform reflected only from substrate 40 and then comparing it to a second waveform reflected from thin film 42 on top of substrate 40.

The phase change is computed as is well known in the art by taking the Fourier transform of superimposed waveform 46+49 and converting to polar coordinates to obtain a value for the phase of the waveform in radians. The phase value corresponding to the output phase value is then subtracted from the input phase value. The waveform for input (unreflected) radiation beam 16 can be derived by impinging radiation beam 16 directly on EO sensor 32 without first reflecting it off sample 20 or, in the alternative, by reflecting radiation beam 16 at a small incidence angle $\theta_1$ which induces no phase change. Taking the Fourier transform of the input and output waveforms and converting to polar coordinates also provides values for amplitude of the waveforms. The amplitude of the output (reflected) waveform divided by the amplitude of the input (unreflected) waveform equals the field reflectance.

In practice, because the exact Brewster angle of the thin film is unknown before evaluation, the waveform change is monitored as a function of the incident angle and the phase shift is extracted using Fresnel equations. According to the Fresnel equations, the field reflectances $r_1$ and $r_2$ from the first and second interfaces, respectively, are a function of $n_1$, $n_2$, $n_3$, $\theta_1$, $\theta_2$, and $\theta_3$, as defined with reference to FIG. 3. In the calculations of the field reflectance and the phase change, multiple reflections between the two interfaces, neglected in FIGS. 3 through 5B for illustrative purposes, are taken into account. The field reflectance $|r_t|$ and the phase retardation Θ can thus be described by:

$$|r_t| = \sqrt{\frac{r_1^2 + r_2^2 + 2r_1 r_2 \cos\left(\frac{4\pi n_2 d \cos(\theta_2)}{\lambda}\right)}{1 + r_1^2 r_2^2 + 2r_1 r_2 \cos\left(\frac{4\pi n_2 d \cos(\theta_2)}{\lambda}\right)}} \quad (1)$$

and $$\Theta = \tan^{-1}\left[\frac{r_2 \sin\left(\frac{4\pi n_2 d \cos(\theta_2)}{\lambda}\right)}{r_1 + r_2 \cos\left(\frac{4\pi n_2 d \cos(\theta_2)}{\lambda}\right)}\right] - \tan^{-1}\left[\frac{r_1 r_2 \sin\left(\frac{4\pi n_2 d \cos(\theta_2)}{\lambda}\right)}{1 + r_1 r_2 \cos\left(\frac{4\pi n_2 d \cos(\theta_2)}{\lambda}\right)}\right] \quad (2)$$

where d is the thickness of thin film 42 and λ is the wavelength of the THz radiation beam 16, and field reflectances $r_1$ and $r_2$ are as follows:

$$r_1 = \frac{n_2\cos\theta_1 - n_1\cos\theta_2}{n_2\cos\theta_1 + n_1\cos\theta_2} \quad (3)$$

$$r_2 = \frac{n_3\cos\theta_2 - n_2\cos\theta_3}{n_3\cos\theta_2 + n_2\cos\theta_3}. \quad (4)$$

Using Snell's law for $r_1$ and $r_2$:

$$n_1 \sin\theta_1 = n_2 \sin\theta_2 = n_3 \sin\theta_3 \quad (5)$$

$\theta_2$ and $\theta_3$ can be expressed in terms of $\theta_1$:

$$\theta_2 = \sin^{-1}\left(\frac{n_1}{n_2}\sin\theta_1\right) \quad (6)$$

$$\theta_3 = \sin^{-1}\left(\frac{n_1}{n_3}\sin\theta_1\right). \quad (7)$$

Substituting equations (6) and (7) into equations (1) through (4), and equations (3) and (4) into equations (1) and (2), $|r_t|$ and $\Theta$ can be expressed as a function of the primary incidence angle $\theta_1$, the thickness d of thin film 42, and the indices of refraction $n_1$ of air 41 and $n_3$ of substrate 40—all of which are known. The index of refraction $n_2$ for thin film 42 remains as the variable for which the equation can be solved. For a given substrate type, the index of refraction at the wavelength to be evaluated, if unknown, may be first calculated by determining the Brewster angle of substrate 40 for that wavelength.

Thus, the index of refraction and dielectric constant can be determined in accordance with the method of the present invention by using the system described above to measure the phase change and field reflectance for a plurality of incident angles within a range of angles that includes the Brewster's angle of thin film 42. The Fresnel equations (1) and (2) above, as converted to functions of incident angle $\theta_1$ with thin film index of refraction $n_2$ as the only unknown, are then solved for iterative values of $n_2$ to provide curves for phase change and field reflectance as a function of $\theta_1$. The index of refraction $n_2$ that provides the curves having the best mathematical fit for the measured field reflectance and phase change data is thus the index of refraction for thin film 42 at the desired frequency.

The following example is included to more clearly demonstrate the overall nature of the invention. This example is exemplary, not restrictive, of the invention.

EXAMPLE

To determine the FIR-Brewster angle reflection of a sample, such as sample 20 as shown in FIGS. 1 and 3, the reflection of the waveform from a Si wafer was first measured at the desired frequency. This analysis was performed at a frequency of 925 GHz, the main spectral position of the FIR pulse (0.2–2.0 THz) generated in the experiment. A laser having a pulse frequency of 82 MHz and a data acquisition system 39 having a lock-in amplifier with a 300 ms sampling frequency were used so that each datapoint for each length of delay stage 11 represented an average value of a set of redundant data for that position. A delay stage having 25 nm resolution was used.

Figure 6:
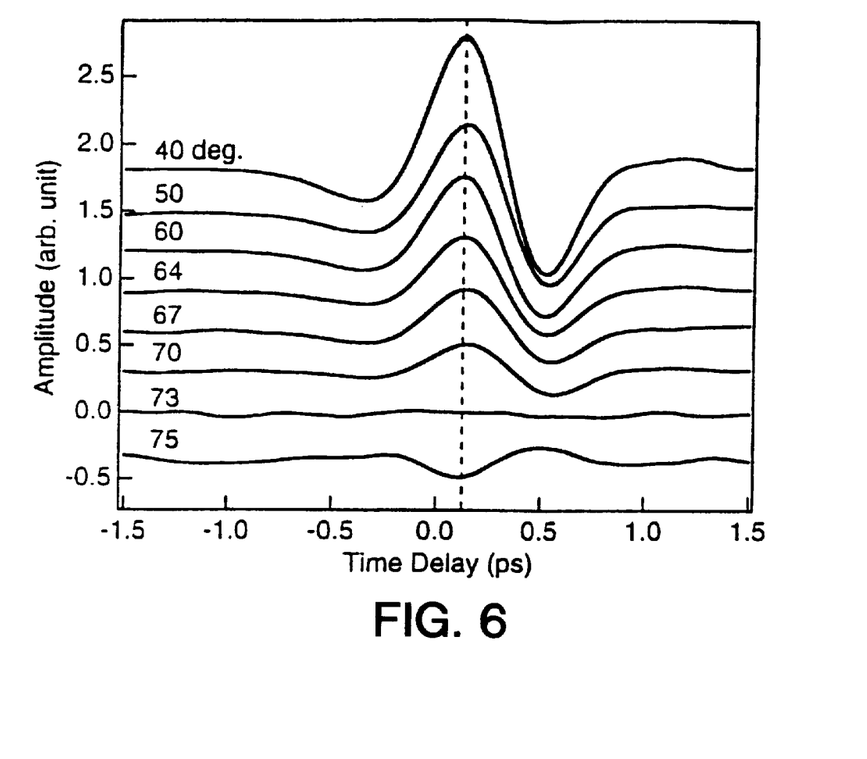
FIG. 6 is a plot depicting waveforms of a FIR reflection from a silicon substrate at different primary incidence angles near the Brewster angle, showing amplitude in arbitrary units and phase changes in picoseconds.
Figure 7:
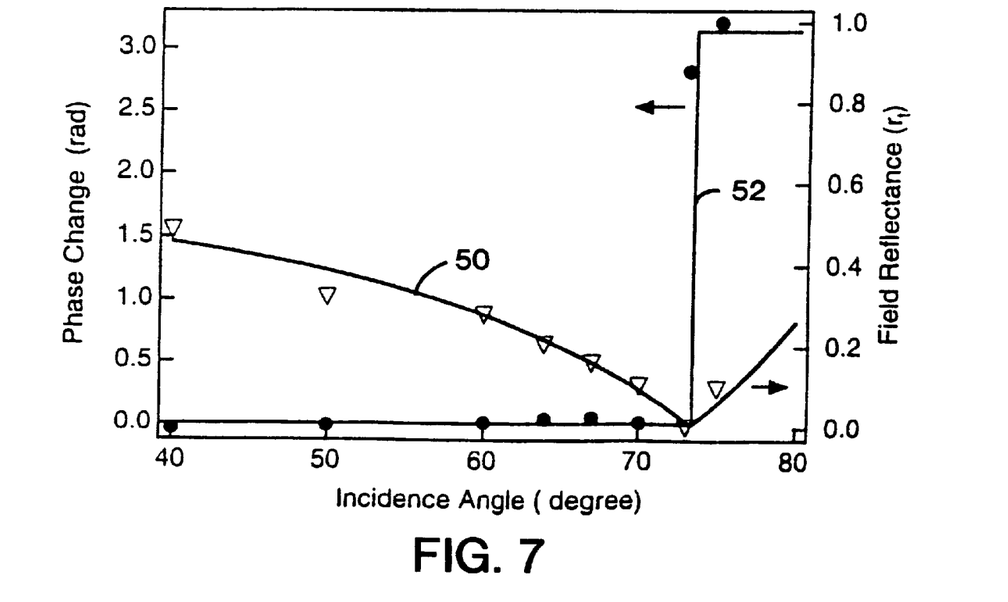
FIG. 7 is a plot of the field reflectance and relative phase change in radians of the main spectral component as a function of the incidence angles of FIG. 6 in degrees and corresponding curve fits calculated using Fresnel equations.

FIG. 6 shows the relative amplitude of reflected waveforms at different incidence angles, with a dashed vertical line provided as a guide line. As expected, no reflection is observed at an incidence angle of 73 degrees, which corresponds to the Brewster angle for Si. FIG. 7 graphically depicts the phase change (filled circles) and field reflectance (unfilled triangles) with respect to normal incidence, obtained using Fourier analysis as a function of the incidence angle on the Si wafer as described above. A sharp phase flip is shown at the Brewster angle at 73 degrees. The best fit for Fresnel equations (1) and (2), shown by solid lines 50 and 52, respectively, gives a value of 11.56 for the dielectric constant of Si and an index of refraction of $n_{si}=3.4\pm0.1$. The zero reflectance shown by line 50 and the sharp phase flip shown by line 52 at the Brewster angle of 73 degrees in FIG. 7 imply that negligible dispersion exists for Si in the overall frequency range investigated, an implication confirmed by reported research with reflective free-space time-domain techniques.

Next, the properties were investigated of a fluorinated poly(arylether) thermoplastic polymer thin film with a low dielectric constant. The tested material is manufactured, and sold under the trademark FLARE, by AlliedSignal Inc. of Sunnyvale, Calif. The FLARE material has a dielectric constant $\kappa=2.8$ (measured in the 1 MHz range) and is being investigated as, among other uses, an interlevel dielectric for ultra-large scale integration (ULSI).

Figure 8:
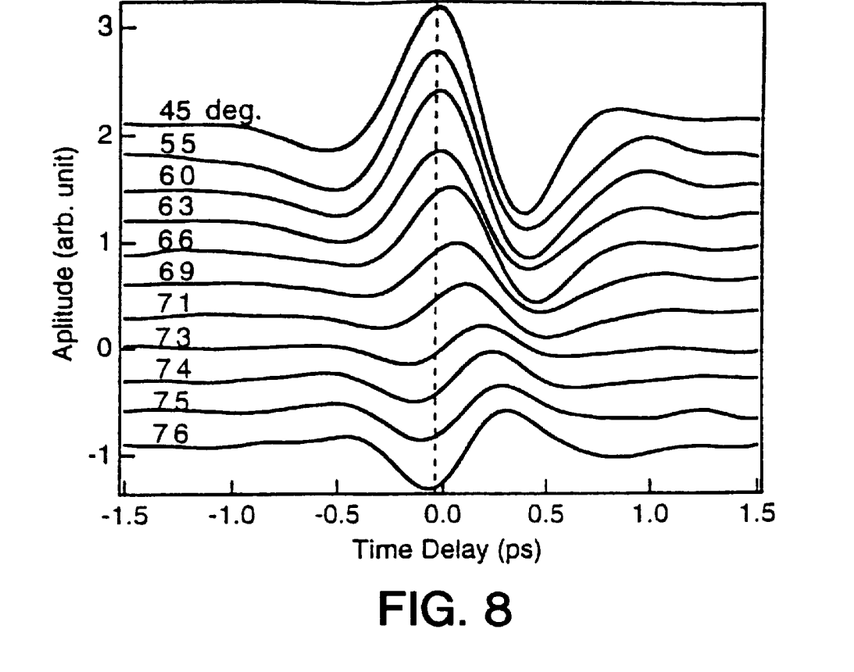
FIG. 8 is a plot depicting waveforms of a FIR reflection from a 3.27 μm FLARE film on a silicon (Si) wafer at different primary incidence angles near the Brewster angle, showing amplitude and phase changes.
Figure 9:
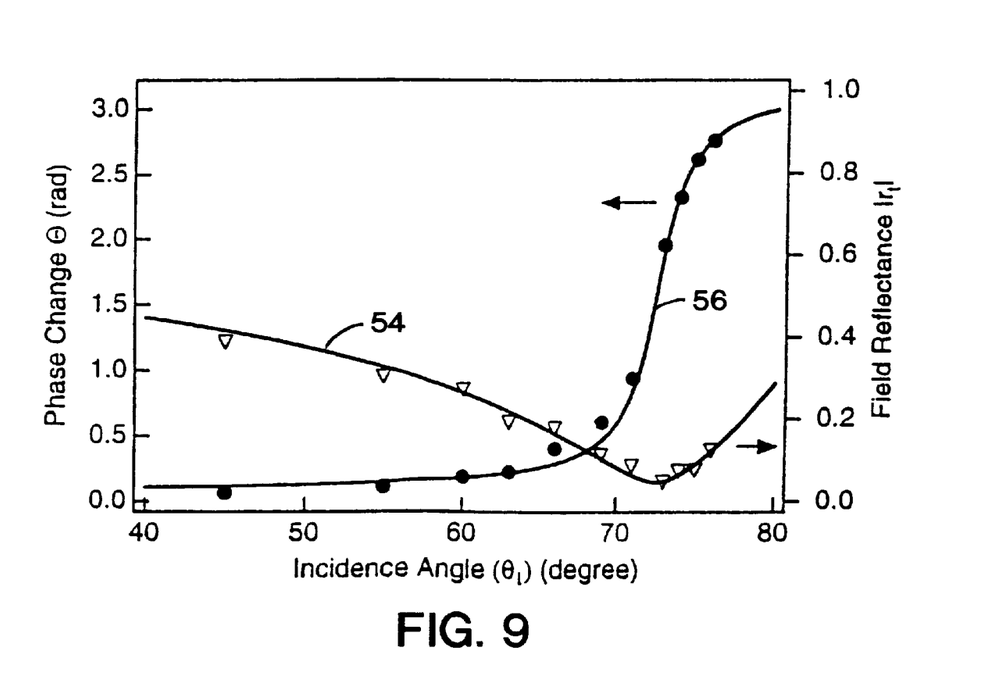
FIG. 9 is a plot of the measured field reflectance and relative phase change in radians of the main spectral component as a function of the incidence angles of FIG. 8 in degrees and corresponding curve fits calculated using Fresnel equations.

The FLARE film investigated was spin-coated on a Si wafer to a thickness of 3.27 μm. FIGS. 8 and 9 show the waveforms of the FIR pulse depicted in the same manner as in FIGS. 6 and 7, respectively. In contrast to the results obtained for the Si wafer shown in FIG. 7, the phase shift as shown in FIG. 9 occurs gradually as the incidence angle is varied around the Brewster angle for Si. A significant change of the field reflectance amplitude is also observed which, unlike FIG. 7, does not vanish at any angle. This non-vanishing amplitude and the gradual phase shift imply a situation similar to that illustrated in FIG. 5B. Thus, the air-to-FLARE interface 44 and FLARE-to-Si interface 45 have different Brewster angles.

Starting from the negligible dispersion of Si, results can be compared with calculations based on the Fresnel equations for a single frequency at 925 GHz. As is well known in the art, $\lambda=c/v$, where c is the speed of light ($3\times10^8$ m/s) and v is the frequency in hertz. The wavelength ($\lambda$) of a 925 GHz frequency pulse is 0.324 mm. Therefore, the 3.27 μm thickness of the FLARE film being measured in this example is slightly greater than approximately $0.01\lambda$. The validity of the equations may be demonstrated for FLARE by comparison with the experimental data. It is assumed that absorption can be neglected in both the FLARE and the silicon substrate. The phase and the amplitude of the measured waveforms were fit using Fourier transformation, with $n_2$ as the fitting parameter. The value of $n_{si}$, as obtained from the measurement of the Si substrate above, was used for the value of $n_3$. Because of the long wavelength of FIR waves, phase shift in the thin film resulting from group delay of the FIR pulse is assumed to be negligible. The experimental values of the phase (filled circles) and field reflectance amplitude (unfilled triangles) as a function of $\theta_1$ are shown in FIG. 9 together with the results of the best fit (solid lines 54 and 56, respectively) calculated from equations (1) and (2) as modified by equations (3) through (8) to be a function of $\theta_1$. The experimental data as well as the calculated fit of line 56 clearly show the relaxed phase flip in contrast to the sharp phase flip as shown in FIG. 7 for the bulk Si.

From the best fit, a dielectric constant of $2.8\pm0.1$ can be calculated for the FLARE polymer. Both the phase shift and amplitude are fitted very well by this value, even through the Fresnel equations are based on a single frequency. This agreement of the experimental data with the curves fit supports the acceptable validity of the calculations based on a single frequency. Moreover, this finding implies a negligible dispersion for the FLARE material in the frequency range investigated. Interestingly, the dielectric constant as measured by the present invention in the FIR range is comparable to that of 2.8 at 1 MHz within experimental error.

METHOD SUMMARY

Thus, as illustrated by the above example, and applicable to any thin film to be studied by the method of the present invention, the index of refraction $n_2$ (and thus the dielectric constant $\kappa = n_2^2$ of thin film 42 on a substrate 40 for a desired frequency having a corresponding wavelength $\lambda$ larger than thickness d of the thin film may be determined by the method of this invention. This method comprises the steps discussed below with reference to FIGS. 1 through 9. First, desired-frequency radiation beam 16 and reference pulse $P_2$ are impinged upon thin film 42 on substrate 40 at an incident angle $\theta_1$ in free space, creating reflected beam 16' and reflected pulse $P_2'$ from the incident beams. The delay between reflected beam 16' and reflected pulse $P_2'$ is varied, such as by varying the length of delay stage 11, until a complete waveform, such as waveform 49, of reflected beam 16' is characterized.

Next, a measured phase change and measured field reflectance are calculated from complete waveform 49 of reflected output desired-frequency beam 16' at incident angle $\theta_1$ with respect to the complete waveform 46 of reflected input desired-frequency beam 16, such as by taking the Fourier transforms of the waveforms and converting the transforms to polar coordinates. These steps are repeated for a plurality of incident angles $\theta_1$ in a range of angles that include the Brewster's angle for thin film 42. Repeating these steps thus creates a dataset of measured phase changes and a dataset of measured field reflectances for the plurality of incident angles $\theta_1$, such as is illustrated by filled circles and unfilled triangles, respectively, of FIG. 9.

Finally, index of refraction $n_2$ for thin film 42 is determined by iteratively calculating a calculated phase change $\Theta$ and a calculated field reflectance $|r_t|$ at each of the plurality of incident angles $\theta_1$ for one or more indices of refraction, such as by using equations (1) through (8) as provided above. The index of refraction for the thin film at the test frequency is the index of refraction that provides the best mathematical curve fit for both the measured phase change and the measured field reflectance datasets for the plurality of incident angles $\theta_1$. Examples are curve fits 56 and 54, respectively, as shown in FIG. 9.

Generally, the lower the frequency or the thinner the film to be measured, the more critical the signal-to-noise ratio in the waveform. Signal-to-noise ratio is generally maximized by maximizing the stability of the laser system and the precision of incident angle resolution. All solid-state laser systems provide maximum stability. Homogeneity of the film layer affects spatial fluctuation of the phase difference.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A non-contact method for determining at least one of the index of refraction and dielectric constant of a thin film with a thickness on a substrate at a desired frequency having a corresponding wavelength longer than the thickness of the thin film, the method comprising:

(a) simultaneously impinging upon the thin film on said substrate at an incident angle in free space an input desired-frequency pulse having a first wavelength and a first duration and an input reference pulse having a second wavelength shorter than said first wavelength and a second duration shorter than said first duration, creating a reflected output desired-frequency pulse and a reflected output reference pulse;

(b) modulating the reflected output reference pulse by the reflected output desired-frequency pulse;

(c) detecting the reflected output reference pulse with a photo detector; and (d) repeating steps (a)–(c) over a plurality of delay times between said input desired-frequency pulse and said input reference pulse until a complete field waveform of said reflected output desired-frequency pulse is characterized;

(e) measuring a measured phase change and a measured field reflectance from said complete field waveform of said reflected output desired-frequency pulse at said incident angle with respect to a complete field waveform of said input desired-frequency pulse;

(f) repeating steps (a)–(e) for a plurality of incident angles in a range of angles, said range encompassing a Brewster's angle for said thin film, thus creating a first dataset of measured phase changes and a second dataset of measured field reflectances for said plurality of incident angles; and (g) identifying the index of refraction for said thin film by iteratively calculating a calculated phase change and a calculated field reflectance for each said incident angle at one or more indices of refraction and selecting the index of refraction that provides a best mathematical curve fit for both said first and second datasets.

2. The method of claim 1 wherein the calculated phase change and calculated field reflectance are calculated using a set of Fresnel equations.

3. The method of claim 2 wherein the set of Fresnel equations includes:

$$|r_t| = \sqrt{\frac{r_1^2 + r_2^2 + 2r_1 r_2 \cos\left(\frac{4\pi n_2 d \cos(\theta_2)}{\lambda}\right)}{1 + r_1^2 r_2^2 + 2r_1 r_2 \cos\left(\frac{4\pi n_2 d \cos(\theta_2)}{\lambda}\right)}}$$

$$\Theta = \tan^{-1}\left[\frac{r_2 \sin\left(\frac{4\pi n_2 d \cos(\theta_2)}{\lambda}\right)}{r_1 + r_2 \cos\left(\frac{4\pi n_2 d \cos(\theta_2)}{\lambda}\right)}\right] - \tan^{-1}\left[\frac{r_1 r_2 \sin\left(\frac{4\pi n_2 d \cos(\theta_2)}{\lambda}\right)}{1 + r_1 r_2 \cos\left(\frac{4\pi n_2 d \cos(\theta_2)}{\lambda}\right)}\right]$$

wherein:

$$r_1 = \frac{n_2 \cos\theta_1 - n_1 \cos\theta_2}{n_2 \cos\theta_1 + n_1 \cos\theta_2}$$

$$r_2 = \frac{n_3 \cos\theta_2 - n_2 \cos\theta_3}{n_3 \cos\theta_2 + n_2 \cos\theta_3}$$

$$n_1 \sin\theta_1 = n_2 \sin\theta_2 = n_3 \sin\theta_3$$

and:

$|r_t|$ represents the calculated field reflectance,
$\Theta$ represents the calculated phase change, d represents the thickness of the thin film, λ represents the wavelength of the desired-frequency pulse, $\theta_1$ represents the incident angle of the desired-frequency pulse to a first interface between said free space and said thin film and, $\theta_2$ represents a resultant angle at which said desired-frequency pulse is refracted by said first interface to a second interface between said thin film and said substrate, $\theta_3$ represents a resultant angle at which said desired-frequency pulse is refracted by said substrate, and $n_1$, $n_2$, and $n_3$ represent indices of refraction for the free space, the thin film, and the substrate, respectively.

4. The method of claim 1 wherein the desired-frequency pulse has a corresponding wavelength greater than about 7 microns.

5. The method of claim 1 wherein the desired-frequency pulse has a corresponding wavelength in a range comprising about 0.1 millimeter to about 1 centimeter.

6. The method of claim 1 wherein the desired-frequency pulse has a gigahertz to terahertz frequency.

7. The method of claim 6 wherein the reference pulse has an optical wavelength.

8. The method of claim 1 wherein the thin film to be measured has a thickness greater than approximately 0.01 times the wavelength of the desired-frequency pulse.

9. The method of claim 1 further comprising determining a dielectric constant for said thin film by calculating the index of refraction squared.

10. The method of claim 1 further comprising:

in step (a) creating a first laser pulse and a second laser pulse, the first laser pulse being an excitation pulse that travels through a variable-length delay stage and impinges upon an emitter that becomes excited and emits said desired-frequency pulse having a p polarization, and the second laser pulse being said reference pulse, having an s polarization;

in step (b): (i) modulating the reflected reference pulse by the reflected desired-frequency pulse using an electro-optical sensor that creates a linearly-polarized electro-optical resultant pulse; (ii) polarizing said linearly-polarized electro-optical resultant pulse with a quarter waveplate, creating a circularly-polarized electro-optical resultant pulse; (iii) linearly polarizing the circularly-polarized electro-optical resultant pulse in a prism which splits the resultant pulse into an first detectable pulse having s plus p polarized components and a second detectable pulse having s minus p polarized components;

in step (c): (i) detecting the first detectable pulse with a first photo detector and the second detectable pulse with a second photo detector, each photo detector converting the corresponding pulse to electronic information; (ii) subtracting the electronic information corresponding to the second detectable pulse from the electronic information corresponding to the first detectable pulse, resulting in noise-reduced electronic information corresponding to the p polarized component, and storing said noise-reduced electronic information;

in step (d) repeating steps (a) through (c)(ii) with different lengths of said delay stage in step (a) until said noise-reduced electronic information in step (c)(ii) corresponds to said complete field waveform of said reflected output desired-frequency pulse;

and in step (e) calculating a Fourier transform of said complete field waveform of said reflected output desired-frequency pulse and converting said Fourier transform to polar coordinates for computation of said measured field reflectance and said measured phase change with respect to a Fourier transform in polar coordinates of said complete field waveform corresponding to said input desired-frequency pulse.

11. A non-contact method for determining at least one of the index of refraction and the dielectric constant of a thin film with a thickness on a substrate at a desired frequency having a corresponding wavelength longer than the thickness of the thin film, the method comprising:

(a) impinging an input desired-frequency pulse and an input reference pulse upon the thin film on the substrate at an incident angle in free space, creating a reflected output desired-frequency pulse and a reflected output reference pulse from the input pulses, the input pulses being impinged over a plurality of delay times between the input desired-frequency pulse and the input reference pulse such that a complete field waveform of the reflected output desired-frequency pulse is characterized, the desired-frequency pulse having one of a wavelength greater than about 7 microns, a wavelength in a range comprising 0.1 millimeter to about 1 centimeter, a gigahertz to terahertz frequency, or a combination thereof;

(b) measuring a measured phase change and a measured field reflectance from the complete field waveform of the reflected output desired-frequency pulse at the incident angle with respect to a complete field waveform of the input desired-frequency pulse;

(c) repeating steps (a) and (b) for a plurality of incident angles in a range of angles, the range encompassing a Brewster's angle for the thin film, thus creating a first dataset of measured phase changes and a second dataset of measured field reflectances for the plurality of incident angles; and (d) identifying the index of refraction for the thin film by iteratively calculating a calculated phase change and a calculated field reflectance for each of the incident angles at one or more indices of refraction and selecting the index of refraction that provides a best mathematical curve fit for both the first and second datasets.

* * * * *

UNITED STATES PATENT AND TRADEMARK OFFICE
CERTIFICATE OF CORRECTION

PATENT NO.    : 6,057,928
DATED         : May 2, 2000
INVENTOR(S)   : Ming Li et al.

It is certified that error appears in the above-identified patent and that said Letters Patent is hereby corrected as shown below:

Column 1,
Line 5, insert -- The U.S. Government has a paid-up license in this invention and the right in limited circumstances to require the patent owner to license others on reasonable terms as provided for by the terms of Contract No. DE-F607-98 ER62706 awarded by the Department of Energy. --.

Signed and Sealed this

Twenty-seventh Day of September, 2005

JON W. DUDAS
*Director of the United States Patent and Trademark Office*